United States Patent
Morin et al.

(10) Patent No.: US 12,347,173 B2
(45) Date of Patent: Jul. 1, 2025

(54) EYE OPENNESS

(71) Applicant: Tobii AB, Danderyd (SE)

(72) Inventors: Clément Morin, Danderyd (SE);
Joakim Zachrisson, Danderyd (SE);
Jonas Sjöstrand, Danderyd (SE);
Shanker Keshavdas, Danderyd (SE);
Ylva Björk, Danderyd (SE)

(73) Assignee: Tobii AB, Danderyd (SE)

( * ) Notice: Subject to any disclaimer, the term of this patent is extended or adjusted under 35 U.S.C. 154(b) by 186 days.

(21) Appl. No.: 18/175,577

(22) Filed: Feb. 28, 2023

(65) Prior Publication Data

US 2023/0277089 A1    Sep. 7, 2023

(30) Foreign Application Priority Data

Mar. 4, 2022 (SE) .................................. 2250299-1

(51) Int. Cl.
*G06V 10/774* (2022.01)
*G06F 3/01* (2006.01)
*G06V 40/18* (2022.01)

(52) U.S. Cl.
CPC ............ *G06V 10/774* (2022.01); *G06F 3/013* (2013.01); *G06V 40/193* (2022.01)

(58) Field of Classification Search
None
See application file for complete search history.

(56) References Cited

U.S. PATENT DOCUMENTS

| 2007/0071289 A1 | 3/2007 | Takeguchi et al. |
| 2012/0014610 A1* | 1/2012 | Nakashi ............ G06T 7/73 |
| | | 382/195 |

(Continued)

FOREIGN PATENT DOCUMENTS

| CN | 115690892 A | 2/2023 |
| EP | 2416294 A1 | 2/2012 |

(Continued)

OTHER PUBLICATIONS

Swedish Search Report dated Sep. 22, 2022.

(Continued)

*Primary Examiner* — Rodney E Fuller
(74) *Attorney, Agent, or Firm* — Christopher Ignatius Moylan

(57) ABSTRACT

A controller configured to: receive first and second curve data respectively defining first and second curves respectively representative of first and second eyelid edges in an eye image; determine an eye-openness-indicator-line extending from a first intersection point on the first curve to a second intersection point on the second curve by performing an optimisation routine comprising: defining an objective function representative of: an orthogonality of the eye-openness-indicator-line to a first tangent to the first curve at the first intersection point; and an orthogonality of the eye openness indicator line to a second tangent to the second curve at the second intersection point; and adjusting a value of the first intersection point and a value of the second intersection point until at least one termination condition for a value of the objective function is satisfied; and provide an eye openness value based on a length of the eye-openness-indicator-line.

19 Claims, 5 Drawing Sheets

(56) References Cited

U.S. PATENT DOCUMENTS

| | | | |
|---|---|---|---|
| 2018/0246320 A1 | 8/2018 | Rana et al. | |
| 2018/0247119 A1* | 8/2018 | Ryan | A61B 3/113 |
| 2019/0324551 A1 | 10/2019 | Parshionikar et al. | |
| 2020/0218878 A1 | 7/2020 | Mequanint et al. | |
| 2020/0290543 A1 | 9/2020 | Saito et al. | |
| 2021/0298595 A1 | 9/2021 | Lai | |
| 2022/0354363 A1* | 11/2022 | Ben-Ami | G06T 7/0016 |
| 2023/0119137 A1* | 4/2023 | Vedantam | G06V 20/597 |
| | | | 340/576 |
| 2023/0419490 A1* | 12/2023 | Koiso | G06V 40/18 |
| 2024/0119594 A1* | 4/2024 | Ben-Ami | A61B 5/163 |

FOREIGN PATENT DOCUMENTS

| | | |
|---|---|---|
| JP | 2009003644 A | 1/2009 |
| WO | 2012/140782 A1 | 10/2012 |
| WO | 2017034861 A1 | 3/2017 |
| WO | 2020197537 A1 | 10/2020 |

OTHER PUBLICATIONS

Fuhl Wolfgang et al. "Fast and robust eyelid outline and apeture detection in real-world scenarious" 2017 IEEE Winter Conference in Applications of Computer Vision (WACV), IEEE, Mar. 24, 2017, doi: 10.1109/wacv.2017.126.

European Search Report in a corresponding European application 23159673.5, published on Sep. 6, 2023.

* cited by examiner

EYE OPENNESS

CROSS-REFERENCE TO RELATED APPLICATION

The present application claims priority to Swedish patent application No. 2250299-1, filed Mar. 4, 2022, entitled "EYE OPENNESS", and is hereby incorporated by reference in its entirety.

FIELD

The present disclosure generally relates to the field of eye tracking. In particular, the present disclosure relates to controllers, algorithms, eye tracking systems and methods for determining an eye openness of an eye.

BACKGROUND

In eye tracking applications, digital images are retrieved of the eyes of a user and the digital images are analysed in order to estimate the gaze direction of the user. The estimation of the gaze direction may be based on computer-based image analysis of features of the imaged eye. One known example method of eye tracking includes the use of infrared light and an image sensor. The infrared light is directed towards the pupil of a user and the reflection of the light is captured by an image sensor.

Many eye tracking systems estimate gaze direction based on identification of a pupil position together with glints or corneal reflections. However, gaze estimation techniques can depend on eye openness—that is a degree of openness of an eye. For example, blink detection can enable the suspension of gaze tracking during a blink. Therefore, accurately determining eye openness can be important for eye tracking systems and methods.

Portable or wearable eye tracking devices have also been previously described. One such eye tracking system is described in U.S. Pat. No. 9,041,787 (which is hereby incorporated by reference in its entirety). A wearable eye tracking device is described using illuminators and image sensors for determining gaze direction.

SUMMARY

According to a first aspect of the present disclosure there is provided a controller configured to:
 receive first curve data defining a first curve representative of a first eyelid edge in an image of an eye;
 receive second curve data defining a second curve representative of a second eyelid edge in the image of the eye;
 determine an eye openness indicator line extending from a first intersection point on the first curve to a second intersection point on the second curve by performing an optimisation routine comprising:
  defining an objective function representative of:
   an orthogonality of the eye openness indicator line to a first tangent to the first curve at the first intersection point; and
   an orthogonality of the eye openness indicator line to a second tangent to the second curve at the second intersection point; and
  adjusting a value of the first intersection point and a value of the second intersection point until at least one termination condition for a value of the objective function is satisfied; and
 provide an eye openness value based on a length of the eye openness indicator line.

The objective function may be based on:
 a first angle between the eye openness indicator line and a normal to the tangent to the first curve at the first intersection point; and
 a second angle between the eye openness indicator line and a normal to the tangent to the second curve at the second intersection point.

The objective function may be based on:
 a dot product of the eye openness indicator line and the tangent to the first curve at the first intersection point; and
 a dot product of the eye openness indicator line and the tangent to the second curve at the second intersection point.

The objective function may be based on a sum of squares of, or a sum of magnitudes of:
 the dot product of the eye openness indicator line and the tangent to the first curve at the first intersection point; and
 the dot product of the eye openness indicator line and the tangent to the second curve at the second intersection point.

The objective function may be further based on the length of the eye openness indicator line.

The optimisation routine may comprise adjusting the value of the first intersection point and the value of the second intersection point to reduce a value of the objective function until the at least one termination condition for the value of the objective function is satisfied.

The at least one termination condition may comprise at least one of:
 the value of the objective function is less than a threshold value;
 the value of the objective function is greater than a threshold value;
 a variation of a fixed number of successive values of the objective function converge within a convergence threshold; and
 a maximum number of iterations of adjusting the value of the first intersection point and the value of the second intersection point have been performed.

The controller may be configured to:
 receive the first curve data as first curve data comprising at least three first data points associated with the first eyelid edge;
 receive the second curve data as second curve data comprising at least three second data points associated with the second eyelid edge;
 curve fit the at least three first data points to define the first curve; and
 curve fit the at least three second data points to define the first curve.

The controller may be configured to curve fit the at least three first data points and the at least three second data points using any of:
 a second order polynomial function;
 a polynomial function of an order higher than second order; an elliptical function;
 a parabolic function;
 a hyperbolic function; and
 a trigonometric function.

The controller may be configured to:
 receive the image of the eye;
 determine the at least three first data points using image processing; and determine the at least three second data points using image processing.

The controller may be configured to:

receive the image of the eye;

label the image of the eye with the eye openness value to provide labelled training data.

The controller may be configured to:

receive a plurality of eye images and first and second curve data associated with each eye image;

determine an eye openness indicator line for each of the plurality of eye images by performing the optimisation routine; and label each eye image with an eye openness value based on a length of the respective eye openness indicator line to provide labelled training data.

The controller may be configured to:

train a machine learning algorithm to output eye openness values in response to eye image inputs using the labelled training data.

According to a second aspect of the present disclosure there is provided a machine learning algorithm trained by any controller disclosed herein.

According to a third aspect of the present disclosure there is provided an eye tracking system comprising:

a memory storing any machine learning algorithm disclosed herein; and a processor configured to:

receive a further image of an eye; and output an eye openness value by processing the image of the eye using the machine learning algorithm.

According to a fourth aspect of the present disclosure there is provided an eye tracking system comprising any controller disclosed herein controller.

According to a fifth aspect of the present disclosure there is provided a method for determining an eye openness value of an image of an eye, the method comprising:

receiving first curve data defining a first curve representative of a first eyelid edge in an image of an eye;

receiving second curve data defining a second curve representative of a second eyelid edge in the image of the eye;

determining an eye openness indicator line extending from a first intersection point on the first curve to a second intersection point on the second curve by performing an optimisation routine comprising:

defining an objective function representative of:

an orthogonality of the eye openness indicator line and a tangent to the first curve at the first intersection point; and an orthogonality of the eye openness indicator line and a tangent to the second curve at the second intersection point; and adjusting a value of the first intersection point and a value of the second intersection point until at least one termination condition for a value of the objective function is satisfied; and providing an eye openness value based on a length of the eye openness indicator line.

The method of claim 15 may further comprise:

receiving the image of the eye;

labelling the image of the eye with the eye openness value to provide labelled training data; and training a machine learning algorithm to output eye openness values in response to eye image inputs using the labelled training data.

According to a sixth aspect of the present disclosure there is provided a machine learning algorithm obtainable by any method disclosed herein.

According to a seventh aspect of the present disclosure there is provided a head-mounted device comprising any eye tracking system disclosed herein.

According to an eight aspect of the present disclosure there is provided one or more non-transitory computer-readable storage media storing computer-executable instructions that, when executed by a computing system, causes the computing system to perform any method disclosed herein.

According to a ninth aspect of the present disclosure there is provided a controller configured to:

receive first curve data defining a first curve representative of a first eyelid edge of an image of an eye;

receive second curve data defining a second curve representative of a second eyelid edge of the image of the eye;

determine an eye openness indicator line extending from a first point on the first curve to a second point on the second curve by selecting the first point and the second point based on:

an orthogonality of a resultant first angle between the eye openness indicator line and a tangent to the first curve at the first point; and an orthogonality of a resultant second angle between the eye openness indicator line and a tangent to the second curve at the second point; and provide an eye openness value based on a length of the eye openness indicator line.

There may be provided a computer program, which when run on a computer, causes the computer to configure any apparatus, including a circuit, controller or device disclosed herein or perform any method disclosed herein. The computer program may be a software implementation, and the computer may be considered as any appropriate hardware, including a digital signal processor, a microcontroller, and an implementation in read only memory (ROM), erasable programmable read only memory (EPROM) or electronically erasable programmable read only memory (EEPROM), as non-limiting examples. The software may be an assembly program.

The computer program may be provided on a computer readable medium, which may be a physical computer readable medium such as a disc or a memory device, or may be embodied as a transient signal. Such a transient signal may be a network download, including an internet download. There may be provided one or more non-transitory computer-readable storage media storing computer-executable instructions that, when executed by a computing system, causes the computing system to perform any method disclosed herein.

BRIEF DESCRIPTION OF THE DRAWINGS

One or more embodiments will now be described by way of example only with reference to the accompanying drawings in which.

DETAILED DESCRIPTION

Figure 1:
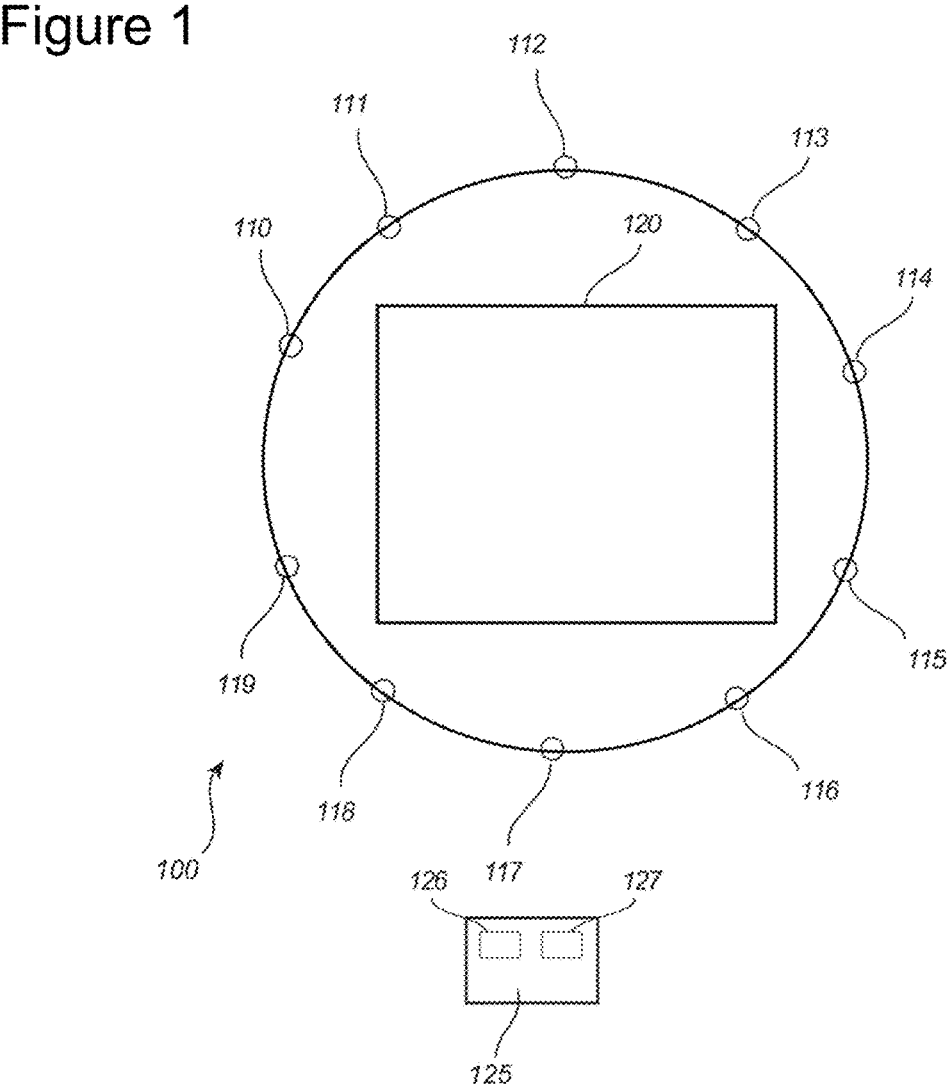
FIG. 1 shows a schematic view of an eye tracking system which may be used to capture a sequence of images that can be used by example embodiments of the present disclosure.

FIG. 1 shows a simplified view of an eye tracking system 100 (which may also be referred to as a gaze tracking system) in a head-mounted device in the form of a virtual or augmented reality (VR or AR) device or VR or AR glasses or anything related, such as extended reality (XR) or mixed reality (MR) headsets. The system 100 comprises an image sensor 120 (e.g. a camera) for capturing images of the eyes of the user. The system may optionally include one or more illuminators 110-119 for illuminating the eyes of a user, which may for example be light emitting diodes emitting light in the infrared frequency band, or in the near infrared frequency band and which may be physically arranged in a variety of configurations. The image sensor 120 may for example be an image sensor of any type, such as a complementary metal oxide semiconductor (CMOS) image sensor or a charged coupled device (CCD) image sensor. The image sensor may consist of an integrated circuit containing an array of pixel sensors, each pixel containing a photodetector and an active amplifier. The image sensor may be capable of converting light into digital signals. In one or more examples, it could be an Infrared image sensor or IR image sensor, an RGB sensor, an RGBW sensor or an RGB or RGBW sensor with IR filter.

The eye tracking system 100 may comprise circuitry or one or more controllers 125, for example including a receiver 126 and processing circuitry 127, for receiving and processing the images captured by the image sensor 120. The circuitry 125 may for example be connected to the image sensor 120 and the optional one or more illuminators 110-119 via a wired or a wireless connection and be co-located with the image sensor 120 and the one or more illuminators 110-119 or located at a distance, e.g. in a different device. In another example, the circuitry 125 may be provided in one or more stacked layers below the light sensitive surface of the light sensor 120.

The eye tracking system 100 may include a display (not shown) for presenting information and/or visual stimuli to the user. The display may comprise a VR display which presents imagery and substantially blocks the user's view of the real-world or an AR display which presents imagery that is to be perceived as overlaid over the user's view of the real-world.

The location of the image sensor 120 for one eye in such a system 100 is generally away from the line of sight for the user in order not to obscure the display for that eye. This configuration may be, for example, enabled by means of so-called hot mirrors which reflect a portion of the light and allows the rest of the light to pass, e.g. infrared light is reflected, and visible light is allowed to pass.

While in the above example the images of the user's eye are captured by a head-mounted image sensor 120, in other examples the images may be captured by an image sensor that is not head-mounted. Such a non-head-mounted system may be referred to as a remote system.

In an eye tracking system, a gaze signal can be computed for each eye of the user (left and right). The quality of these gaze signals can be reduced by disturbances in the input images (such as image noise) and by incorrect algorithm behaviour (such as incorrect predictions). A goal of the eye tracking system is to deliver a gaze signal that is as good as possible, both in terms of accuracy (bias error) and precision (variance error). For many applications it can be sufficient to deliver only one gaze signal per time instance, rather than both the gaze of the left and right eyes individually. Further, the combined gaze signal can be provided in combination with the left and right signals. Such a gaze signal can be referred to as a combined gaze signal.

Figure 2:
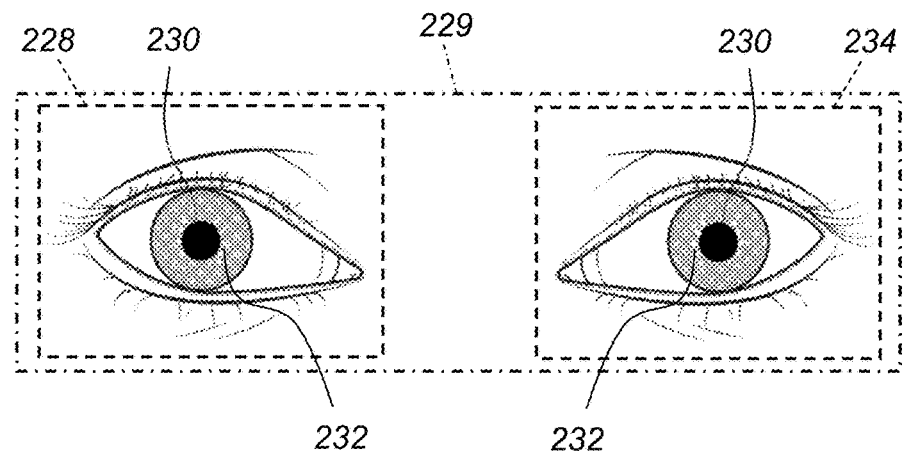
FIG. 2 shows an example image of a pair of eyes.

FIG. 2 shows a simplified example of an image 229 of a pair of eyes, captured by an eye tracking system such as the system of FIG. 1. The image 229 can be considered as including a right-eye-image 228, of a person's right eye, and a left-eye-image 234, of the person's left eye. In this example the right-eye-image 228 and the left-eye-image 234 are both parts of a larger image of both of the person's eyes. In other examples, separate image sensors may be used to acquire the right-eye-image 228 and the left-eye-image 234.

The system may employ image processing (such as digital image processing) for extracting features in the image. The system may for example identify a position of the pupil 230 in the one or more images captured by the image sensor. The system may determine the position of the pupil 230 using a pupil detection process. The system may also identify corneal reflections 232 located in close proximity to the pupil 230. The system may estimate a corneal centre or eye ball centre based on the corneal reflections 232. For example, the system may match each of the individual corneal reflections 232 for each eye with a corresponding illuminator and determine the corneal centre of each eye based on the matching.

Eye openness is a bio-metric signal used in a large range of applications of eye tracking systems, for example the eye tracking system of FIG. 1. Example applications include behavioural and cognitive research, automotive driver monitoring systems and gaze signal filtering and/or validation.

Figure 3:
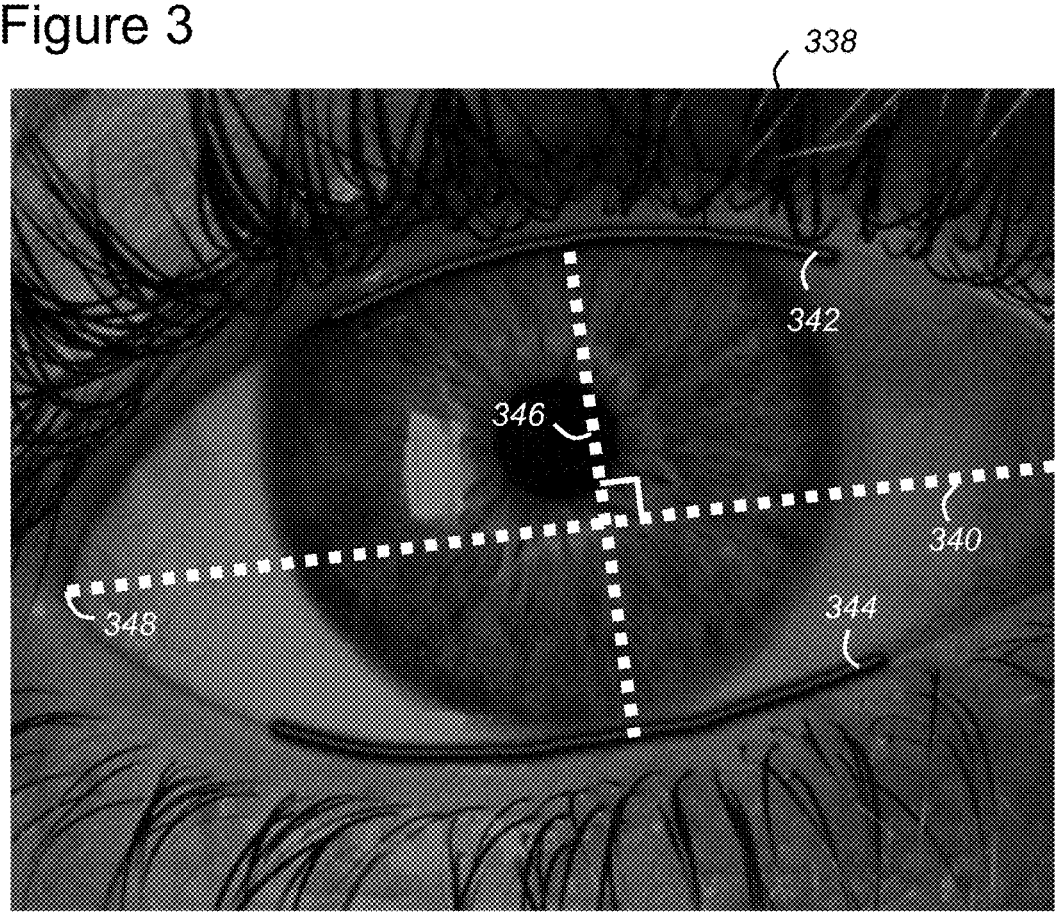
FIG. 3 illustrates an example measure of eye openness.

FIG. 3 illustrates an example measure of eye openness 346 for an image of an eye 338. In this example, eye openness 346 can be defined as a maximum distance between an upper eye lid 342 and a lower eyelid 344 in a direction orthogonal to a horizontal eye-axis 340 connecting a first corner of the eye 348 to a second corner of the eye (not shown). In this context, "eyelid" is the line segment that constitutes the edge visually separating an eyeball and eyelid skin.

Eye tracking systems can use an automated process to determine eye openness, for example, a classic rule-based algorithm or a machine learning (ML) algorithm. An ML algorithm can be trained using eye images labelled (or paired) with ground truth values of eye openness. A rule-based algorithm for determining eye openness may also require ground truth values in order to measure the accuracy of the determination.

For determining the ground truth value of eye openness, acquiring the actual 3D distance (a value represented in millimeters) between eyelids is challenging. Obtaining an accurate 3D distance can require a non-intrusive device that can measure the 3D distance with precision and accuracy. An alternative approach is to determine eye openness in the (2D) image domain in which the ground truth eye openness can be annotated. For example, an image of an eye 338 can be labelled with an eye openness value 346 measured according to the example of FIG. 3 and a plurality of such labelled images can be used as training data for the ML algorithm. The image domain approach works particularly well for a small or zero perspective between the camera and the eye. However, larger perspectives can be corrected using camera parameters, a camera-eye distance, a size of the eye in the image etc.

Image labelling in the image domain is typically performed manually and relies on subjective human judgement in relation to the eyelid edges 342, 344 and the maximum vertical distance 346. Annotating the largest orthogonal distance between upper and lower eyelids 342, 344 can be difficult and inconsistent and relies heavily on the subjective assessment of the person annotating the image. The annotation requires the annotator to visually find a pair of points where the eye is the most open, which is time consuming and difficult. As a result, the image labelling process is time consuming and the resulting training data and ML algorithm can lack accuracy and repeatability.

The disclosed apparatus and methods can determine eye openness for eye images. The apparatus and methods can infer image domain eye openness from an image of an eye or from a set of landmark points along the upper and lower eyelid edges 342, 344 of the image. The apparatus and methods can advantageously provide accurate and repeatable values of eye openness for eye images. The eye openness values may be used for labelling training data for an eye openness ML algorithm and/or for determining eye openness values in an eye tracking system.

Figure 4:
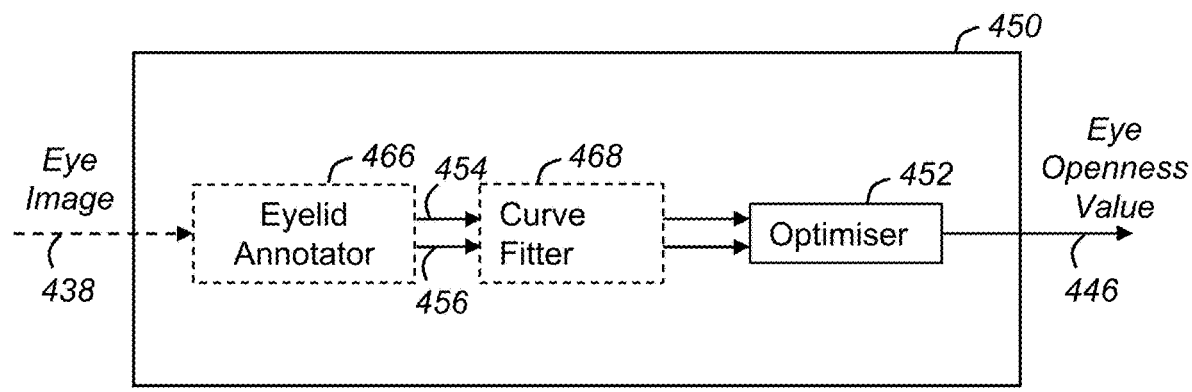
FIG. 4 illustrates a controller for providing an eye openness value of an image according to an embodiment of the disclosure.
Figure 5:
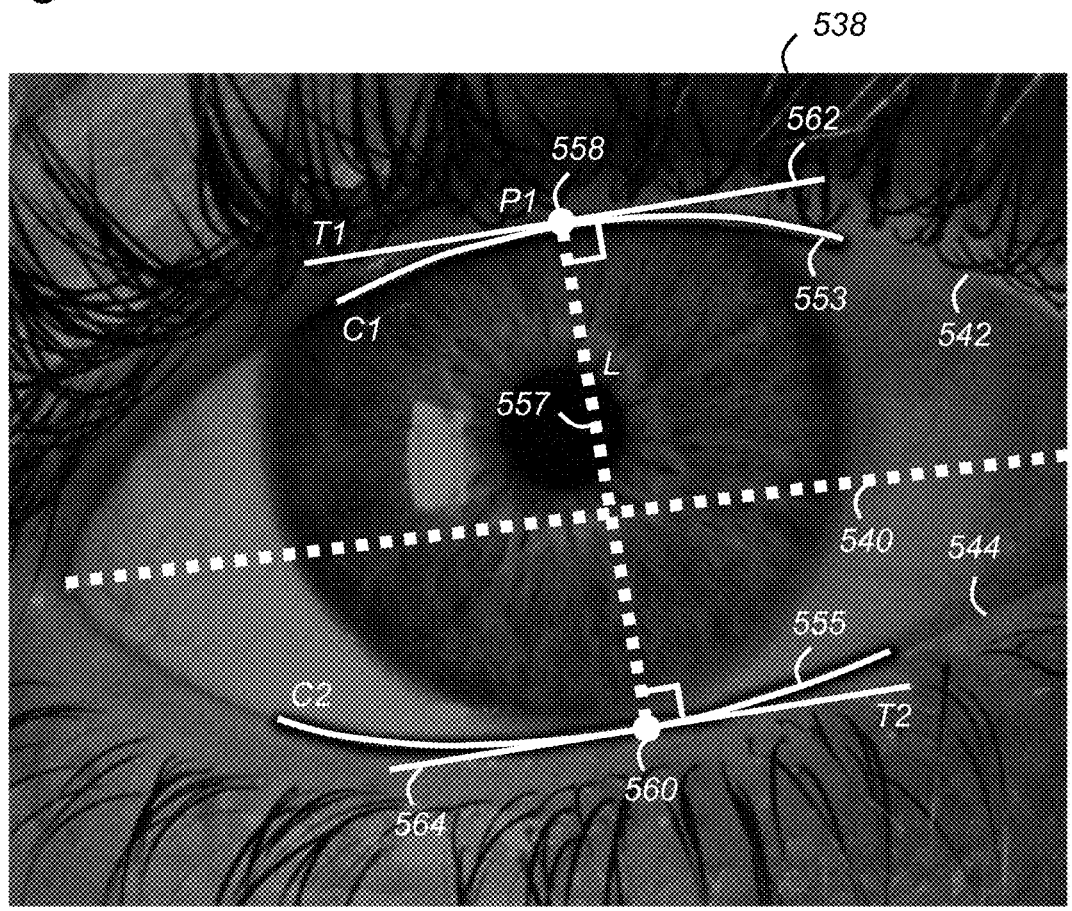
FIG. 5 illustrates the geometrical relationships used by the controller of FIG. 4.

FIG. 4 illustrates a controller 450 for providing an eye openness value 446 of an image of an eye 438, according to an embodiment of the present disclosure. The controller 450 is described with reference to the image of the eye 538 in FIG. 5.

In this example, the controller 450 comprises an optimiser 452 configured to receive first curve data 454 and second curve data 456 (optionally via a curve fitter 468). The first and second curve data 454, 456 respectively define a first curve, C1, 553 and second curve, C2, 555 each representative of a respective first (upper) eyelid edge 542 and second (lower) eyelid edge 544 in/of the image of the eye 438, 538. The optimiser 452 is configured to determine an eye openness indicator line, L, 557 extending from a first intersection point, P1, 558 on the first curve 553 to a second intersection point, P2, 560 on the second curve 555 by performing an optimisation routine. The optimisation routine comprises first defining an objective function representative of: an orthogonality of the eye openness indicator line 557 to a first tangent, T1, 562 of the first curve 553 at the first intersection point 558; and an orthogonality of the eye openness indicator line 557 to a second tangent, T2, 564 of the second curve 555 at the second intersection point 560. The optimisation routine further comprises adjusting a value of the first intersection point 558 and the second intersection point 560 until at least one termination condition for a value of the objective function is satisfied. For example, the first and second intersection points 558, 560 may be adjusted until a minimum value of the objective function is obtained such that the two angles between eye openness indicator line 557 and the first and second tangents 562, 564 are as close to 90 degrees as possible. Following determination of the eye openness indicator line 557 using the optimisation routine, the controller 450 is configured to provide or output the eye openness value 446 based on a length of the eye openness indicator line 557.

The optimisation routine can find the pair of first and second intersection points, P1, P2 on the first and second curves, C1, C2 such that the eye openness indicator line extending between them, L(P1, P2), is orthogonal (or as close to orthogonal as possible) to the first and second tangents, T1, T2, where T1 equals the tangent to C1 at P1 and T2 equals the tangent to C2 at P2.

The optimisation routine may comprise:

(i) Defining the objective function as a residual function R(P1, P2) based on the angles between the eye openness indicator line, L(P1,P2), and the first and second tangents, T1, T2. For example, the objective function may be based on: a dot product of the eye openness indicator line, L(P1,P2), and the first tangent T1; and a dot product of the eye openness indicator line, L(P1, P2), and the second tangent, T2. For example, the residual function may be based on (or equal to) the sum of the squares of the two dot products:

$$R(P1,P2)=f((T1 \cdot L)^2+(T2 \cdot L)^2)$$

When the first and second tangents T1, T2 are both orthogonal to the eye openness indicator line, L(P1, P2), the residual function will be zero. In some examples, the sum of the squares of the dot products may comprise a weighted sum. In some examples, each dot product may be normalised by dividing by the magnitudes of the eye openness indicator line and the respective tangent. In some examples, the residual function may be based on or equal to a sum of the magnitudes of the two dot products.

A further example residual function may be based on: a first angle, α1, between the eye openness indicator line, L(P1,P2), and a normal to the first tangent, T1; and a second angle, α2, between the eye openness indicator line, L(P1,P2), and a normal to the second tangent, T2. In some examples, the residual function may be based on (or equal to) the sum of the magnitudes of the two angles:

$$R(P1,P2)=f(|\alpha 1|+|\alpha 2|)$$

When the first and second tangents T1, T2 are both orthogonal to the eye openness indicator line, L(P1, P2), the residual function will be zero.

(ii) Using a numerical optimiser to find values of the first and second intersection points, P1, P2 that minimize the objective function R(P1,P2). The numerical optimiser may comprise known optimisation algorithms, for example, a Nelder-Mead method, a hill climb/descent routine or any other known optimisation method. The optimisation method may comprise iteratively adjusting the values of the first and second intersection points, P1, P2, and computing the resultant objective function to determine a minimum of the objective function. The adjusted values of the first and second intersection points, P1(n), P2(n), for a particular iteration may be selected based on the first and second intersection points, P1(n−1, n−2, . . . ), P2(n−1, n−2, . . . ) and the resulting objective function values R(P1(n−1, n−2, . . . ), P2(n−1, n−2, . . . )) from one or more previous iterations.

Under typical conditions (where the area between the first and second eyelids 542, 544 is convex and the eyelid curvatures are small enough) the eye openness indicator line segment L(P1,P2) between those intersection points P1, P2 that minimize the orthogonality-based objective function R will also be a diameter of the largest circular disk that fits between the eyelids. Therefore, the controller 450 is configured to provide the eye openness value 446 based on the length of the eye openness indicator line 557. For example, the controller 450 may provide the eye openness value 446 based on a magnitude of the length of the eye openness indicator line, IL(P1,P2)I.

In some examples, the objective function may be further based on the length of the eye openness indicator line 557. For example, the sum (or weighted sum) in the above objective functions may comprise an additional term inversely proportional to the length of the eye openness indicator line 557, such that the objective function will reduce as the length of the eye openness indicator line increases.

Although the objective functions and optimisation routines described above relate to minimising a residual function (or loss function), it will be appreciated that the objective function may also be defined such that the optimisation routine determines a maximum value of the objective function. For example, the objective function may be based on a sum of the magnitudes of the angles complementary to $\alpha 1$ and $\alpha 2$—that is a sum of the magnitudes of: an angle between the eye openness indicator line 557 and the first tangent 562; and an angle between the eye openness indicator line 557 and the second tangent 564. Such an objective function would have a maximum value of $\pi$ radians. A maximising objective function may also further include a length term in the sum proportional to the length of the eye openness indicator line 557.

The at least one termination condition for the value of the objective function may comprise known termination conditions used in optimisation methods. For example, for residual objective functions (or loss functions) defined for an optimisation routine to minimise the value of the objective function, the at least one termination condition may comprise the value of the objective function being less than a threshold value. For objective functions defined for an optimisation routine to maximise the value of the objective function, the at least one termination condition may comprise the value of the objective function being greater than a threshold value.

The at least one terminating condition may also relate to a convergence of successive iterative values of the objective function. For example, the at least one terminating condition may comprise successive iterative values of the objective function converging such that a variation of a predetermined number of the successive iterative values is less than a convergence threshold. The convergence threshold may correspond to a relative and/or an absolute variation in a fixed number of successive iterative values (e.g. 5 successive iteration values with an absolute variation of $10^{-6}$ or with a relative variation of $10^{-4}$).

The at least one terminating condition may comprise reaching a maximum number of iterations of adjusting the values of the first and second intersection points, 558, 560.

The eye openness indicator line 557 in FIG. 4 is not orthogonal to the horizontal axis 540. This illustrates the limitation of the eye openness measure of FIG. 3 which is limited to eyelid to eyelid distances in a direction orthogonal to the horizontal axis 540. Such a limitation can provide inaccurate or inconsistent values of eye openness for some eyelid edge shapes. In contrast, by defining the eye openness indicator line 557 based on the orthogonality to the two tangents 562, 564, the disclosed apparatus and methods can advantageously provide a more accurate representation of eye openness and allow for a greater anatomical variation in eye shape.

In the example of FIG. 4, the controller 450 comprises an optional curve fitter 468 and the optimiser 452 receives the first curve data 454 and second curve data 456 via the curve fitter 468. In this example, the first curve data 454 comprises at least three first data points (also referred to as landmark points or eyelid landmarks) associated with (i.e. lying on, approximately on or proximal to) the first eyelid edge 542. Similarly, the second curve data 456 comprises at least three second data points associated with the second eyelid edge 544. The first and second data points may be identified or annotated in the eye image 438 manually by a user or automatically using image processing, as discussed further below.

The curve fitter 468 may fit a curve to the at least three first data points to define the first curve 553 and fit a curve to the at least three second data points to define the second curve 555. The curve fitter 468 may fit one or both curves using known curve fitting methods. The curve fitting performed by the curve fitter 468 can advantageously smooth out any annotation errors in the at least three first and second data points. For example, if a user has inaccurately annotated one of the at least three first data points such that it is offset from the first eyelid edge 542, the curve fitting based on the at least two other first data points can compensate for the annotation error. In some examples, the first and second curve data 454, 456 respectively comprise three first and second data points. Three data points has surprisingly been found to provide sufficient accuracy and repeatability in the eye openness value 446 for eye tracking applications. Although more data points can provide an improvement in accuracy and/or repeatability, the improvement is at the expense of extra annotation and processing. In some examples, the number of first data points may differ from the number of second data points. For example, different number of data points may be selected when one eyelid is more difficult to annotate or has an atypical anatomical shape.

The curve fitter 468 may fit one or both curves 553, 555 using a curve function comprising any of: a second order polynomial function; a polynomial function of an order higher than second order; an elliptical function; a circular function; a parabolic function; a hyperbolic function; a trigonometric function or any other known curve function. Using a second order polynomial function (or other function with a single turning point) can advantageously avoid overfitting of the first and second curves 553, 555 and the resulting poor representation of the eyelid edge.

In other examples, the controller 450 may not include a curve fitter and the optimiser 452 may receive the first and second curve data 454, 456 from an external source, such as another controller or processing module or as user input (manual data entry). The optimiser 452 may receive the first and second curve data 454, 456 as equation parameters defining the respective curves (for example, parabolic equation parameters or polynomial equation parameters) or as a set of points for defining each respective curve by interpolation. In such examples, the controller 450 may receive the first and second curve data 454, 456 and may not receive the eye image 438.

Figure 6:
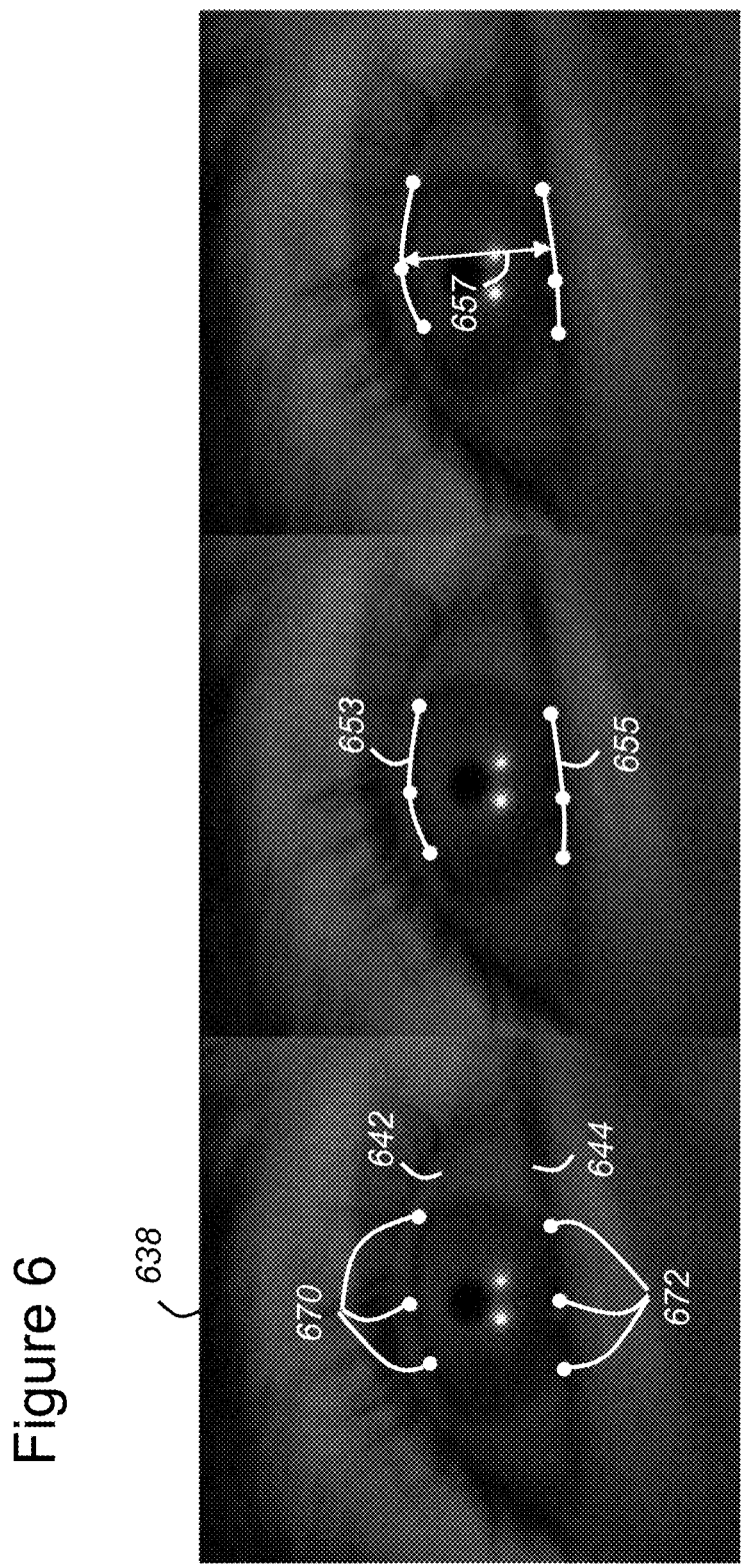
FIG. 6 schematically illustrates operational steps performed by a controller according to an embodiment of the disclosure.

FIG. 6 schematically illustrates the operational steps performed by a controller comprising the curve fitter 468 and the optimiser 452. The operation steps include:
(i) For each of the first (upper) eyelid edge 642 and the second (lower) eyelid edge 644, receive N landmark points 670, 672 associated with the respective eyelid edge. N can be any number>2 and different for the first eyelid edge 642 and the second eyelid edge 644. The N landmark data points for the first eyelid edge 642 comprise at least three first data points 670. The N landmark data points for the second eyelid edge 642 comprise at least three second data points 672.

(ii) Fit 2D first and second curves 653, 655 (for example a circle segment or a polynomial) in the image 638 to the respective N landmark points 670, 672.

(iii) Perform an optimisation routine as described above to determine the eye openness indicator line 657. Provide the eye openness value based on the length of the eye openness indicator line.

Returning to FIG. 4, the controller 450 can comprise an optional eyelid annotator 466 configured to provide the first and second curve data 454, 456 to the curve fitter 468. The eyelid annotator 466 is configured to receive the image of the eye 438. The eyelid annotator 466 may receive the image of the eye 438 from an image sensor, from a memory storage device or from another processing module which performs initial image processing on the image 438 (e.g. noise filtering etc). The eyelid annotator 466 may include an eyelid landmark detection algorithm configured to identify and output landmark points on the first and second eyelid 542, 544. For example, the eyelid annotator 466 may determine the at least three first data points and the at least three second data points using the eyelid landmark detection algorithm.

In other examples, the controller 450 may not include an eyelid annotator and the curve fitter 468 may receive the first and second curve data 454, 456 from an external source, such as another controller or processing module or as user input (landmark points based on manually annotated images). In such examples, the controller 450 may receive the first and second curve data 454, 456 and may not receive the eye image 438.

The controller 450 of FIG. 4 can be used in an eye tracking system in which the controller 450 can provide eye openness values for eye images captured by the eye tracking system for applications including blink detection, alertness detection and gaze filtering. The controller 450 can also be used to provide training data for an eye openness ML algorithm.

Figure 7:
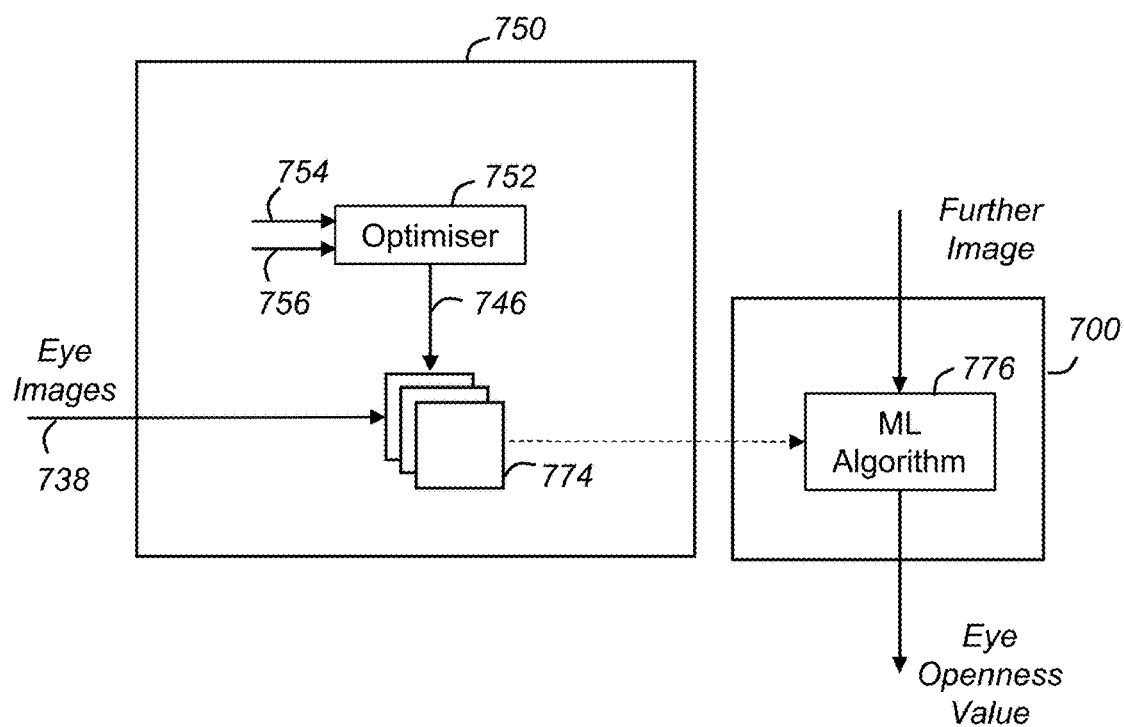
FIG. 7 illustrates another controller for providing an eye openness value and an eye tracking system according to embodiments of the present disclosure.

FIG. 7 illustrates another controller 750 for providing an eye openness value and an eye tracking system 700 according to embodiments of the present disclosure. Features of FIG. 7 that are also present in FIG. 4 have been given corresponding numbers in the 700 series and are not necessarily described again here.

The controller 750 is configured to receive a plurality of eye images 738 and first and second curve data 754, 756 associated with each image. The controller 750 comprises an optimiser 752 which is configured to determine an eye openness indicator line and an eye openness value 746 for each image based on the respective first and second curve data 754, 756, by performing the optimisation routine in the same way as described above in relation to FIGS. 4 and 5.

The controller 750 is configured to label each eye image in the plurality of eye images with the respective eye openness value 746 to provide labelled training data 774. The labelled training data 774 may comprise a plurality of data pairs, each data pair comprising an eye image and an eye openness value corresponding to the eye image. The controller 750 is further configured to train an ML algorithm 776 using the labelled training data. For example, the controller 750 may train a convolutional neural network to determine eye openness values of any image of an eye.

The trained ML algorithm 776 may form part of an eye tracking system 700. The eye tracking system 700 can receive a further image of an eye and output an eye openness value by processing the further image of the eye using the trained ML algorithm 776. In some examples, the eye tracking system 700 may comprise the controller 750.

Figure 8:
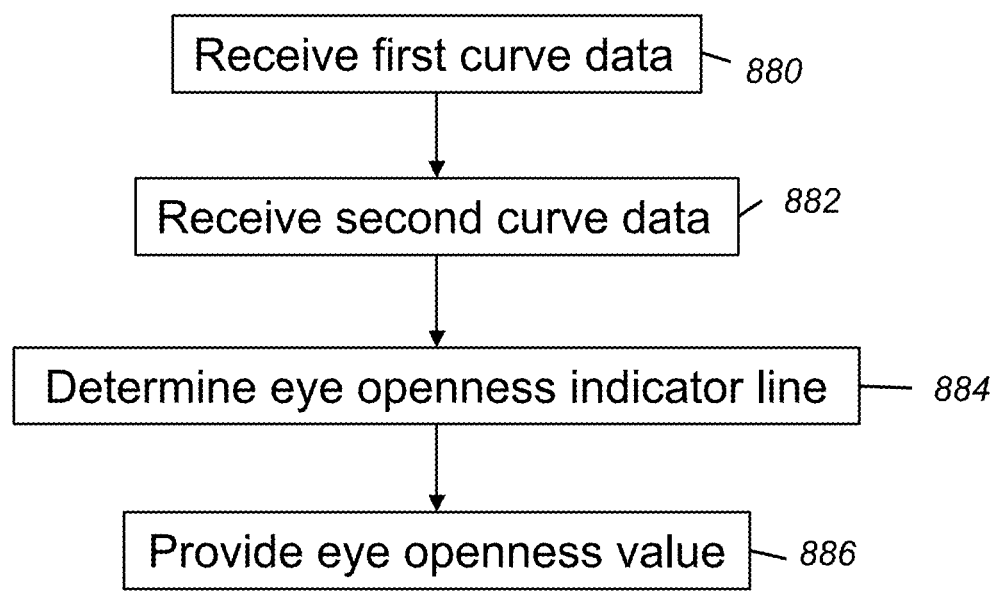
FIG. 8 illustrates schematically a method according to an embodiment of the present disclosure.

FIG. 8 illustrates a method for determining an eye openness value of an image of an eye according to an embodiment of the present disclosure.

Step 880 comprises receiving first curve data defining a first curve representative of a first eyelid edge in an image of an eye. Step 882 comprises receiving second curve data defining a second curve representative of a second eyelid edge of the image of the eye. Step 884 comprises determining an eye openness indicator line extending from a first intersection point on the first curve to a second intersection point on the second curve, using an optimisation routine. The optimisation routine comprises: defining an objective function representative of: an orthogonality of the eye openness indicator line and a tangent to the first curve at the first intersection point; and an orthogonality of the eye openness indicator line and a tangent to the second curve at the second intersection point; and adjusting a value of the first intersection point and a value of the second intersection point until at least one termination condition for a value of the objective function is satisfied. Step 886 comprises providing an eye openness value based on a length of the eye openness indicator line.

Figure 9:
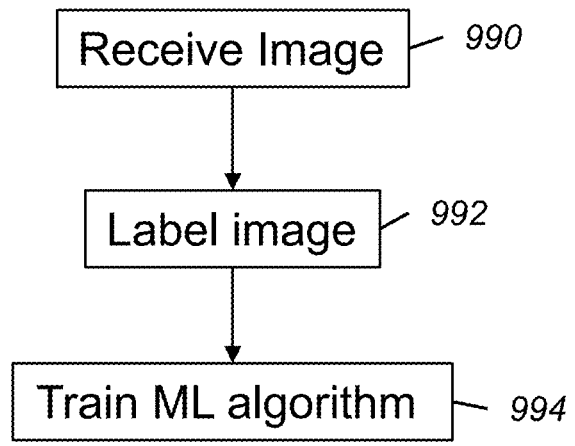
FIG. 9 illustrates schematically a further method according to an embodiment of the present disclosure.

FIG. 9 illustrates a method of training an ML algorithm according to an embodiment of the present disclosure.

Step 990 comprises receiving an image of an eye. Step 992 comprises determining an eye openness value according to the method of FIG. 8 and labelling the image with the eye openness value to provide labelled training data. Step 994 comprises training a machine learning algorithm to output eye openness values in response to eye image inputs using the labelled training data. The trained ML algorithm may be used in an eye tracking system to determine an eye openness value for a further image of the eye captured by the eye tracking system.

The disclosed apparatus and methods can determine eye openness for eye images. The apparatus and methods can infer image domain eye openness from an image of an eye or from a set of landmark points along the upper and lower eyelids of the image. The apparatus and methods can advantageously provide accurate and repeatable values of eye openness for eye images. The eye openness values may be used for labelling training data for an eye openness ML algorithm and/or for determining eye openness values in an eye tracking system.

The disclosed apparatus and methods can have reduced sensitivity to the placement of landmark points. The apparatus and methods can enable an annotator (machine or human) to be less precise when annotating the eyelid edges or the landmark points on the eyelid edge. For example, a human annotator need only identify three or more points along the eyelid edge. There is no requirement to identify the pair of points on the two eyelid edges with the greatest separation orthogonal to the horizontal axis as required using the measure of FIG. 3.

Throughout the present specification, the descriptors relating to relative orientation and position, such as "horizontal", "vertical", "top", "bottom" and "side", are used in the sense of the orientation of the apparatus/device as presented in the drawings. However, such descriptors are not intended to be in any way limiting to an intended use of the described or claimed invention.

It will be appreciated that any reference to "close to", "before", "shortly before", "after" "shortly after", "higher than", or "lower than", etc, can refer to the parameter in question being less than or greater than a threshold value, or between two threshold values, depending upon the context.

The invention claimed is:

1. A controller configured to:
receive first curve data defining a first curve representative of a first eyelid edge in an image of an eye;
receive second curve data defining a second curve representative of a second eyelid edge in the image of the eye;
determine an eye openness indicator line extending from a first intersection point on the first curve to a second intersection point on the second curve by performing an optimization routine comprising:
defining an objective function representative of:
an orthogonality of the eye openness indicator line to a first tangent to the first curve at the first intersection point; and
an orthogonality of the eye openness indicator line to a second tangent to the second curve at the second intersection point; and
adjusting a value of the first intersection point and a value of the second intersection point until at least one termination condition for a value of the objective function is satisfied, wherein the at least one termination condition comprises at least one of:
the value of the objective function is less than a threshold value;
the value of the objective function is greater than a threshold value;
a variation of a fixed number of successive values of the objective function converge within a convergence threshold; and
a maximum number of iterations of adjusting the value of the first intersection point and the value of the second intersection point have been performed; and
provide an eye openness value based on a length of the eye openness indicator line.

2. The controller of claim 1, wherein the objective function is based on:
a first angle between the eye openness indicator line and a normal to the tangent to the first curve at the first intersection point; and
a second angle between the eye openness indicator line and a normal to the tangent to the second curve at the second intersection point.

3. The controller of claim 1, wherein the objective function is based on:
a dot product of the eye openness indicator line and the tangent to the first curve at the first intersection point; and
a dot product of the eye openness indicator line and the tangent to the second curve at the second intersection point.

4. The controller of claim 3, wherein the objective function is based on a sum of squares of, or a sum of magnitudes of:
the dot product of the eye openness indicator line and the tangent to the first curve at the first intersection point; and
the dot product of the eye openness indicator line and the tangent to the second curve at the second intersection point.

5. The controller of claim 1, wherein the optimization routine comprises adjusting the value of the first intersection point and the value of the second intersection point to reduce a value of the objective function until the at least one termination condition for the value of the objective function is satisfied.

6. The controller of claim 1, wherein the controller is configured to:
receive the first curve data as first curve data comprising at least three first data points associated with the first eyelid edge;
receive the second curve data as second curve data comprising at least three second data points associated with the second eyelid edge;
curve fit the at least three first data points to define the first curve; and
curve fit the at least three second data points to define the first curve.

7. The controller of claim 6, wherein the controller is configured to curve fit the at least three first data points and the at least three second data points using any of:
a second order polynomial function;
a polynomial function of an order higher than second order; an elliptical function;
a parabolic function;
a hyperbolic function; and
a trigonometric function.

8. The controller system of claim 6, wherein the controller is configured to:
receive the image of the eye;
determine the at least three first data points using image processing; and
determine the at least three second data points using image processing.

9. The controller of claim 1, wherein the controller is configured to:
receive the image of the eye;
label the image of the eye with the eye openness value to provide labelled training data.

10. The controller of claim 9 configured to:
train a machine learning algorithm to output eye openness values in response to eye image inputs using the labelled training data.

11. A machine learning algorithm trained by the controller of claim 10.

12. An eye tracking system comprising:
a memory storing the machine learning algorithm of claim 11; and
a processor configured to:
receive a further image of an eye; and
output an eye openness value by processing the image of the eye using the machine learning algorithm.

13. A head-mounted device comprising the eye tracking system of claim 12.

14. An eye tracking system comprising the controller of claim 1.

15. A method for determining an eye openness value of an image of an eye, the method comprising:
receiving first curve data defining a first curve representative of a first eyelid edge in an image of an eye;
receiving second curve data defining a second curve representative of a second eyelid edge in the image of the eye;
determining an eye openness indicator line extending from a first intersection point on the first curve to a second intersection point on the second curve by performing an optimization routine comprising:

defining an objective function representative of:

an orthogonality of the eye openness indicator line and a tangent to the first curve at the first intersection point; and an orthogonality of the eye openness indicator line and a tangent to the second curve at the second intersection point; and adjusting a value of the first intersection point and a value of the second intersection point until at least one termination condition for a value of the objective function is satisfied, wherein the at least one termination condition comprises at least one of:

the value of the objective function is less than a threshold value;

the value of the objective function is greater than a threshold value;

a variation of a fixed number of successive values of the objective function converge within a convergence threshold; and a maximum number of iterations of adjusting the value of the first intersection point and the value of the second intersection point have been performed; and providing an eye openness value based on a length of the eye openness indicator line.

16. The method of claim 15 further comprising:

receiving the image of the eye;

labelling the image of the eye with the eye openness value to provide labelled training data; and training a machine learning algorithm to output eye openness values in response to eye image inputs using the labelled training data.

17. A machine learning algorithm obtainable by the method of claim 16.

18. An eye tracking system comprising:

a memory storing the machine learning algorithm of claim 17; and a processor configured to:

receive a further image of an eye; and output an eye openness value by processing the image of the eye using the machine learning algorithm.

19. One or more non-transitory computer-readable storage media storing computer-executable instructions that, when executed by a computing system, causes the computing system to perform the method of claim 15.

* * * * *